United States Patent
Mayeaux

(10) Patent No.: US 7,752,928 B1
(45) Date of Patent: Jul. 13, 2010

(54) MODULAR SAMPLE CONDITIONING SYSTEM

(75) Inventor: Donald P. Mayeaux, St. Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 108 days.

(21) Appl. No.: 11/695,517

(22) Filed: Apr. 2, 2007

Related U.S. Application Data

(60) Provisional application No. 60/789,620, filed on Apr. 3, 2006.

(51) Int. Cl.
*G01N 1/00* (2006.01)

(52) U.S. Cl. .......................................... 73/863
(58) Field of Classification Search ............... 73/863; 137/884
See application file for complete search history.

(56) References Cited

U.S. PATENT DOCUMENTS

| | | | |
|---|---|---|---|
| 2,871,887 A | 2/1959 | Obrebski et al. | 138/111 |
| 3,631,881 A | 1/1972 | Bowditch | 137/271 |
| 3,831,953 A | 8/1974 | Leibfritz et al | 277/637 |
| 4,112,768 A | 9/1978 | Holland et al. | 73/863.24 |
| 4,572,521 A | 2/1986 | Drost et al. | 277/643 |
| 4,800,763 A | 1/1989 | Hakkers et al. | 73/863 |
| 4,834,946 A | 5/1989 | Levin | 422/101 |
| 4,865,811 A | 9/1989 | Newton et al. | 422/81 |
| 4,891,117 A | 1/1990 | Gardner, Sr. | 204/253 |
| 4,928,541 A | 5/1990 | Toon et al. | 73/864.63 |
| 4,957,008 A | 9/1990 | Proni et al. | 73/864.83 |
| 5,367,912 A | 11/1994 | Demachi | 73/863.73 |
| 5,442,969 A | 8/1995 | Troutner et al. | 73/863.71 |
| 5,637,792 A | 6/1997 | Kimura et al. | 73/114.71 |
| 5,713,582 A | 2/1998 | Swensen et al. | 277/312 |
| 5,841,036 A | 11/1998 | Mayeaux | 73/863 |
| 6,122,825 A | 9/2000 | Mayeaux | 29/890.12 |
| 6,186,506 B1 | 2/2001 | Kionoshita | 277/313 |
| 6,457,717 B1 | 10/2002 | Mayeaux | 277/312 |
| 6,892,762 B2 | 5/2005 | Porter | 137/884 |
| 2002/0124961 A1 | 9/2002 | Porter et al. | 156/345.33 |
| 2004/0173270 A1* | 9/2004 | Harris et al. | 137/884 |
| 2006/0185746 A1* | 8/2006 | Doyle | 137/884 |

* cited by examiner

*Primary Examiner*—Hezron Williams
*Assistant Examiner*—Tamiko D Bellamy
(74) *Attorney, Agent, or Firm*—Joseph T Regard, Ltd plc

(57) ABSTRACT

An on-stream sample collection and conditioning system, which is easier to construct, implement, maintain, and is more cost efficient then existing systems. The preferred embodiment of the present invention contemplates a modular system adaptable to a variety of diverse sample conditioning requirements. The system having incorporated a seamless piece having a surface for docking multiple sample conditioning components and having a system of internal passages to provide fluid flow between sample conditioning components. The preferred embodiment of the present invention also contemplates a modular system containing essentially the entire sample conditioning components required for one or more fluid streams.

26 Claims, 13 Drawing Sheets

MODULAR SAMPLE CONDITIONING SYSTEM

The present application claims the benefit of provisional patent application Ser. No. 60/789,620 filed Apr. 3, 2006, entitled MODULAR SAMPLE CONDITIONING SYSTEM, listing as inventor Donald P. Mayeaux.

TECHNICAL FIELD OF THE INVENTION

The present invention relates to on-stream sample and conditioning systems, and more particularly a modular on-stream sample collection and conditioning system adaptable to a variety of diverse sample conditioning requirements, utilizing a seamless base having an outer surface for mounting multiple sample conditioning components, the system utilizing internal passages formed therein to provide fluid flow and/or electrical power and or communications means (i.e., electrical wire, fiber optic, or the like) between said sample conditioning components. Suitable connectors (i.e., fluid, electrical, light, etc) may be provided at the docking areas to facilitate ease in installation and removal of the conditioning components, or extensions or accessories associated with the system. The preferred embodiment of the present invention contemplates a modular system containing the complete sample conditioning component package for one or more fluid streams.

BACKGROUND OF THE INVENTION

Third party systems for conditioning fluid samples have generally required the design and assembly of a complex system of multiple modular bases, to produce a sample conditioning system for a single sample fluid stream.

Examples of such systems include the Parker's Intraflow system, Swagelok® MPC system (see for example U.S. Pat. No. 6,938,644) and the Circor Tech modular substrate sampling system. Each of these systems requires a working knowledge of how the interconnecting base and passage structure must be designed to perform a desired sample conditioning fluid circuit. Further, the resulting structure is difficult to design and troubleshoot due to the complex fluid passage constructed created in multiple planes.

The current state of the art may be summarized as utilizing two basic approaches. The original or older approach, still in widespread use, is to mount individual sample conditioning components to a plate or base board and provide fluid interconnection as required between sample conditioning components with tubing, piping, and fittings. This results in bulky systems with limited performance due to large internal and dead volume created by this method of fluid interconnections.

The other approach, which is gradually making its way, is the modular sample conditioning systems previously referenced. Also, refer to Mayeaux U.S. Pat. No. 5,841,036 (the contents of which are incorporated herein by reference), which leads the way for this emerging technology. While the current art modular approach provides a more compact and better functioning sample conditioning system than previous systems, they generally require considerably greater thought and expertise to assemble, install, and implement.

Reference is made to U.S. Pat. No. 6,892,762, which employs a technique to form a fluid delivery system, and to U.S. Pat. No. 2,871,887 which employs a technique to form a hydraulic fluid circuit and to U.S. Pat. No. 3,631,881, which employs a technique to form closed conduits for transmitting fluid pressures between pneumatic components.

GENERAL SUMMARY DISCUSSION OF THE INVENTION

The present invention relates to the analysis of fluids in a fluid process stream, such as implemented by petrochemical plants, refineries, pipelines, etc, and in particular to an on-stream sample collecting and conditioning system which is easier to implement, more cost efficient, and more reliable than existing systems.

The preferred embodiment of the present system contemplates a modular system for receiving sample conditioning components or the like which is adaptable to a variety of diverse configurations and criteria, the system having incorporated therein a first and second base plates each formed of a seamless sheet of stainless steel. It is noted that stainless steel is indicated as an exemplary material, and is not intended to be limiting, as many materials would likewise function, some in superior fashion, depending upon the application and operating environment.

The first and second seamless sheets of stainless steel are bonded or fused together to form a single sheet having internal fluid passages and a docking surface for mounting multiple sample conditioning components.

The fluid passages provide fluid flow between sample conditioning components and are formed by incorporating grooves in one or more of the surfaces of the first and second base pieces prior to bonding. Grooves forming fluid passages when first and second base pieces are bonded or fused together to form a single fused base board.

Access apertures formed in the plates extending from one or more surfaces of the fused base board to the internal fluid passages are provided complete the fluid path between sample conditioning components, which are fastened to one or more mounting surfaces of the fused base board in fluidic communication with the internal passages of the fused base board.

In this manner, essentially all of the sample conditioning components required for proper conditioning of a sample fluid stream may be interconnected, as desired, without the use of tubing, piping, or fittings. Another important feature of this approach is to build sample conditioning systems in which the internal passages can be formed to suit the particular flow requirements between two sample conditioning components.

For example, the passageways for the larger fluid flows such as "slip stream" or "by pass" fluid stream can be made with a larger cross sectional area than the passageways for the conditioned fluid flowing to an analyzer. The shape and smoothness of the passage surfaces can also be custom designed for specific applications.

The preferred embodiment of the present invention also contemplates the internal passages formed as previously described in the fused base boards to also function as conduits for the passage and protection of electrical and electronic conductors or communication cables, which may be required for sensors or other components requiring power, or communication wiring for the sample conditioning components mounted thereto.

The preferred embodiment of the present invention also contemplates the formation of passages, as previously described, to provide a means for heating, cooling, and or vaporizing sample fluid and/or said base board module.

Unlike the third party systems, the present invention further contemplates a useful system for conditioning a fluid sample which does not require the design and assembly of a complex system of multiple modular bases to produce a sample conditioning for a single sample fluid stream as in the case with current modular sample conditioning bases.

The present invention by way of comparison contemplates the mounting of conditioning components on a plane surface upon which fluid paths can be traced by way of painted or etched lines and symbols similar to the methods utilizing in electronic circuit boards. The plane surface of the fused base board facilitates mounting and temperature control. For example, the fused board can be heated with a plate or ribbon heater, or via fluid circulating through a passage, or via thermoelectric heating or cooling mediums situated in a predesignated passage, since it has a flat surface in a single plane.

There are many applications requiring similar or identical sample fluid conditioning. An object of the present invention is to provide a single piece base module suitable for docking essentially all of the conditioning components required for a common application, and containing an internal structure of the required fluid interconnections between said conditioning components.

The process of bonding or fusing plates with passages formed by sealing of grooves has been utilized for forming fluid circuit suitable for use in heat exchanges, vaporizers, and fluid distribution systems for the electronic industries. What is novel in the present invention is the utilization of this fused or bonded plate and grooving technique to form a unique and near ideal, if not ideal, fluid path for a sample conditioning circuit dedicated for a specific application and not requiring the end user to design and assemble a large array of parts.

A second embodiment of the present invention further contemplates a system for fluid passages to surround areas where fluid leaks may potentially occur, such as connection points between a sample conditioning component and the surface of the fused base board in a manner that, should a fluid leak occur, it will be captured and routed to a suitable location. This approach provides safety when dealing with flammable and/or toxic fluids and will provide a means to monitor for leaks. For example, the leaking fluid captured as described may be visually or electronically monitored by several current art techniques.

Yet a third embodiment of the present invention contemplates the use of one or more passages for the purpose of flowing non-sample fluids, such as actuation gas for actuation of stream switching valves. Refer to FIGS. 2, 8, and 9.

The present system thereby eliminates the need for designing and building a base system from a large number of "erector set" base parts, providing a system which is easier to fabricate, troubleshoot and operate. The system also provides less panel space than other types of modular systems and can be fitted with cooling or heating components (for heating a ribbon or plate heater can be used) as required.

The single board modular construction could be prefabricated with all the components mounted and tested to users specification before delivery, whereupon the system may be simply installed with nominal effort. The present system can be easily serviced by the customer, as defective components may be easily removed and replaced, or the entire system field replaced by the customer.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figure 1:
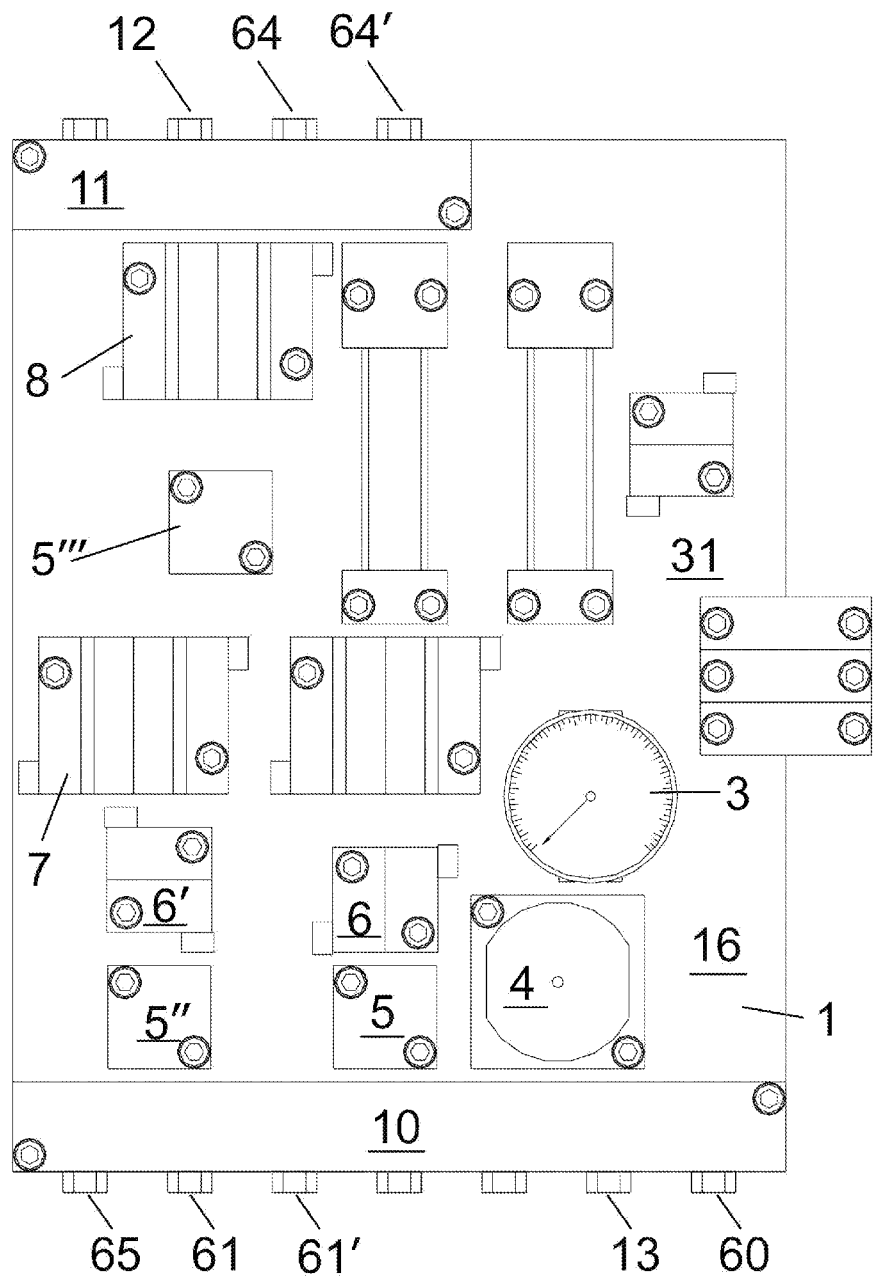
FIG. 1 is a top view of the modular sample conditioning system of the present invention, illustrating fluid conditioning component modules mounted to a modular base configured for one sample stream and a calibration gas.

Design, Fabrication, and Method of Use of the Fused Base Board Sample Conditioning System The preferred embodiment of the present invention includes a novel apparatus for providing modular interconnection of sample conditioning systems, as well as a method of assemblage therefore. The system of the present invention simplifies fabrication, reduces construction time, improves performance, is safer in operation, and essentially eliminates fugitive sample fluid emissions to the environment.

Utilizing the method of the present invention, conditioning components such as valves, pressure regulators, flow meters, and filters and the like can be readily assembled into a functional sample conditioning system, upon a prefabricated modular base, said base having a fluid schematic situated therethrough which may be dedicated to a particular application or configuration, or may be flexible in design to allow for multiple alternative applications, depending upon the needs and the components mounted thereto.

The system utilizes a unique modular base unit design, whereupon the individual conditioning components are mounted.

The base unit 1 comprises a first, top plate 16 having upper outer 31 surface and a lower inner 31' surface, as shown in FIGS. 1, 3, 4, and 5. The inner 31' surface has formed thereupon a series of grooves 17, 17' reflecting a predetermined flow configuration. The depth 32 and width 32' of said grooves can vary depending upon the application. For example, a fluid may require a certain flow rate or have certain physical characteristics which dictate certain passage size or configuration. The passageways can be engineered for maximum efficiency in the layout, providing a clean, dead volume free fluid path. Likewise, the passage may be utilized for a purpose other than fluid flow, such as a passageway for a conductor or optical cable in an electrical or communications application, which may have its own size requirements.

Access apertures 20, 20' are provided through said top plate 16, and are situated and measured to extend from the outer 31 surface of the top plate to intersect with a predetermined groove 17" formed in the bottom, inner 31' surface of the top plate, so as to provide a passageway to or from said top plate for a mounted conditioner assembly (which will be more fully discussed herein), to the groove to which it communicates.

Mounting apertures 18 are provided to mount the conditioning components to the outer surface of the top plate via fasteners or other conventional means known in the art.

Figure 5:
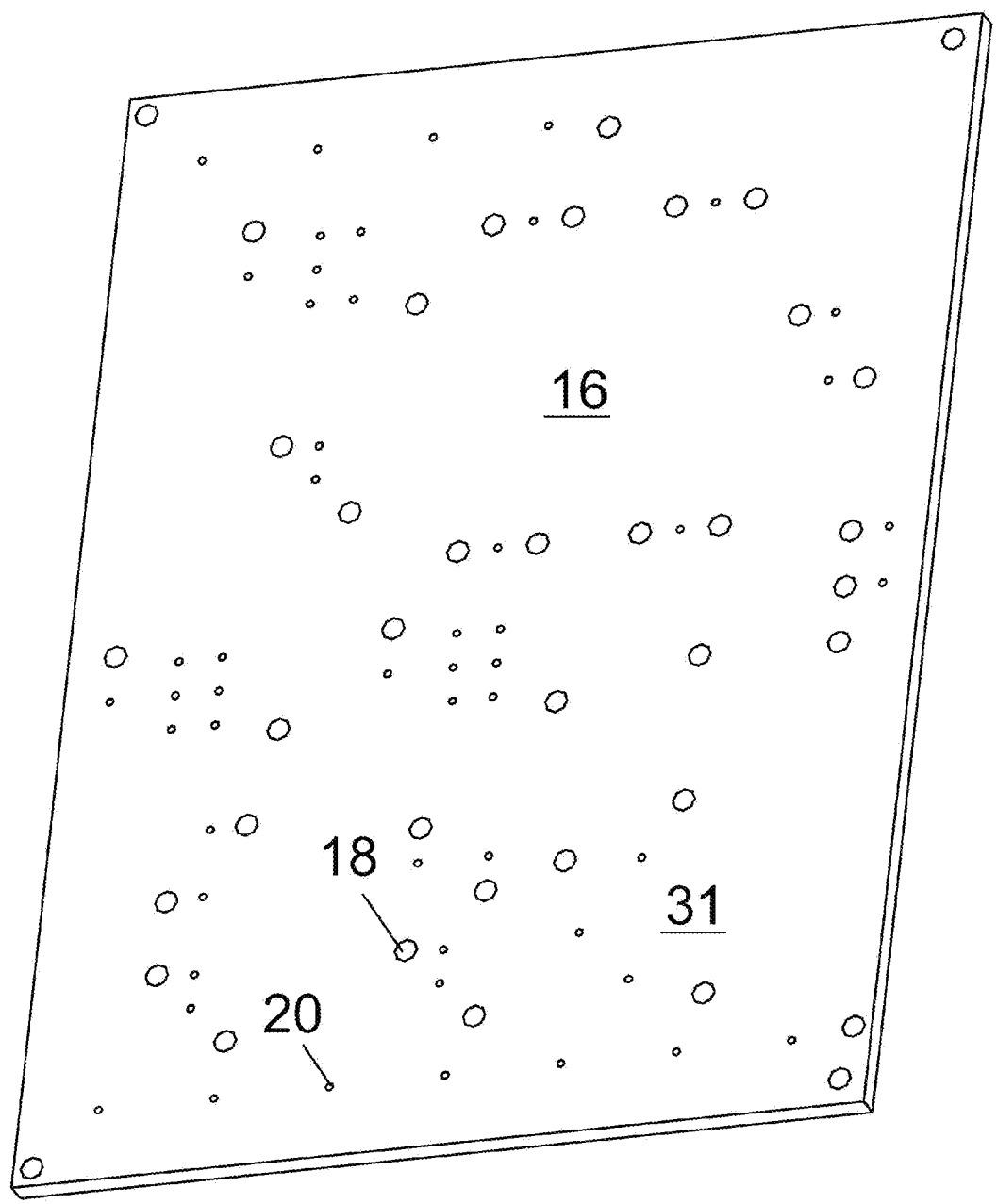
FIG. 5 is an isometric view of the top surface of the top plate forming the modular base of FIG. 3.
Figure 6:
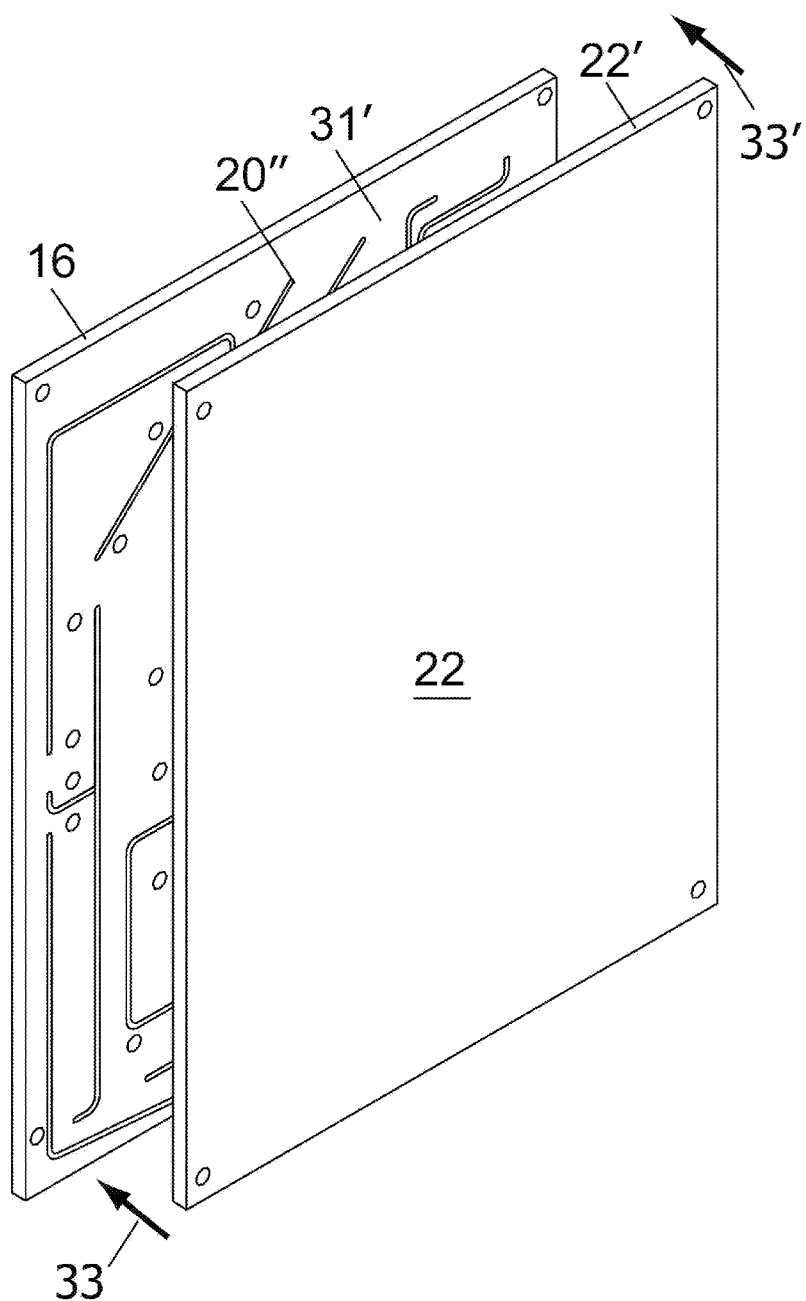
FIG. 6 is illustrates the top and bottom plates of the present invention with one surface of the bottom plate facing and in alignment with the bottom surface of the top plate, positioned for assembly.

FIG. 5 shows the outer 31 mounting surface of the top plate, along with the mounting apertures 18 and access apertures 20 mentioned above. FIG. 6 shows the top 16 and bottom 22 plates with the inner surface 22' of the bottom plate facing and in alignment with the inner surface 31' of the top plate.

Figure 7:
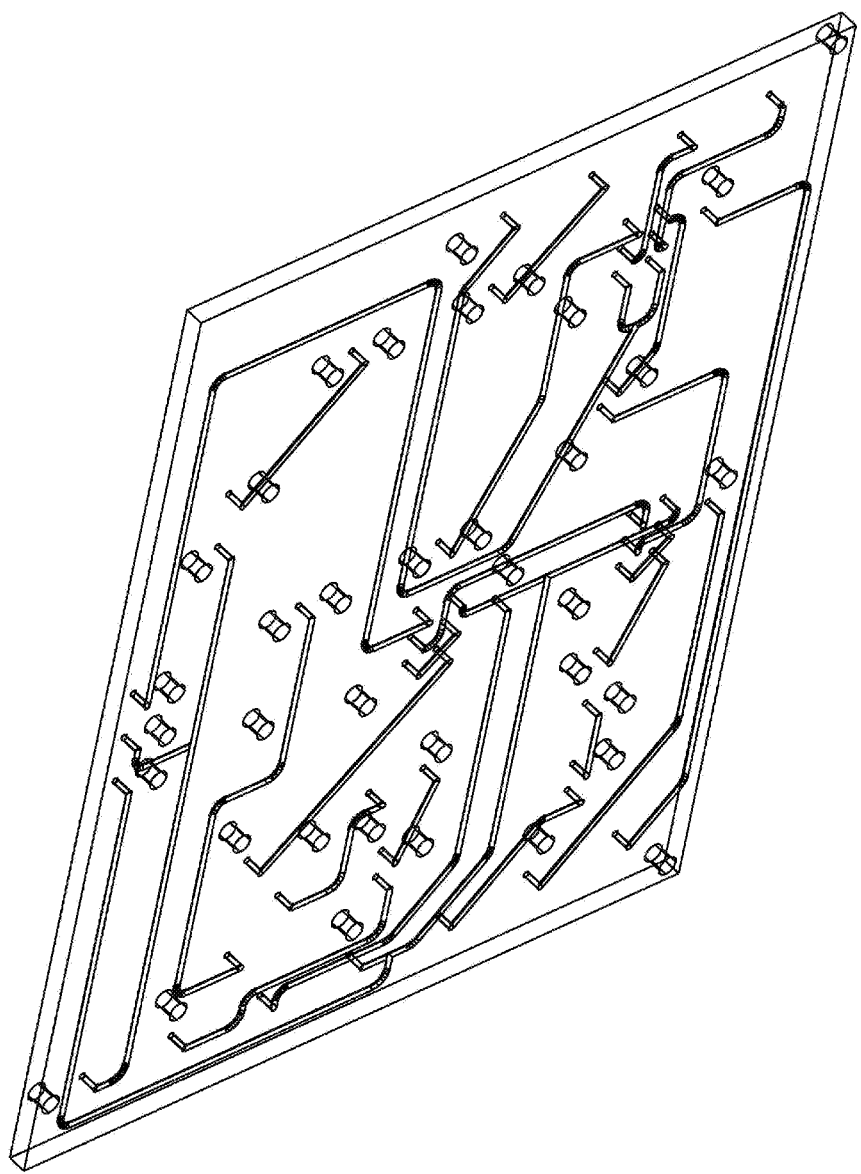
FIG. 7 is a transparent view of the lower surface of the top plate of FIG. 3.

When the top plate (with the grooves formed on its inner surface) and bottom plates are joined 33, 33' and fused together with their respective inner surfaces (31', 22'), in face to face engagement (i.e., stacked) and fused together as such they form a unitary base board which provides a docking surface at the outer surface 31 of the top plate 16, with internal interconnection passages or access apertures 20" (via the grooves such as those grooves 17 formed in the inner surface 31' of the top plate, enclosed by the bottom plate) as shown in FIG. 7.

The top and bottom plates can be constructed preferably of stainless steel; however, many other materials may be utilized, such as plastics, aluminum, and hastoloy, for example. The plates may be fused together by a variety of methods including vacuum brazing process, bonding with adhesives, or mechanically by inserting a thin gasket material with the plates and gaskets forming a sandwich held in place with threaded fasteners.

In general, while for many applications it could be preferable from a cost standpoint to construct a fused board with integrated internal fluid passages as previously described having the top plate's top surface serve as a component docking surface, and the top plate's inner, bottom surface grooved to form passageways, there may be cases where it may be best to form grooves in a upper surface of the bottom plate, which would in effect form an inner surface (with grooves forming fluid conduits) when bonded with the top plate.

Figure 11:
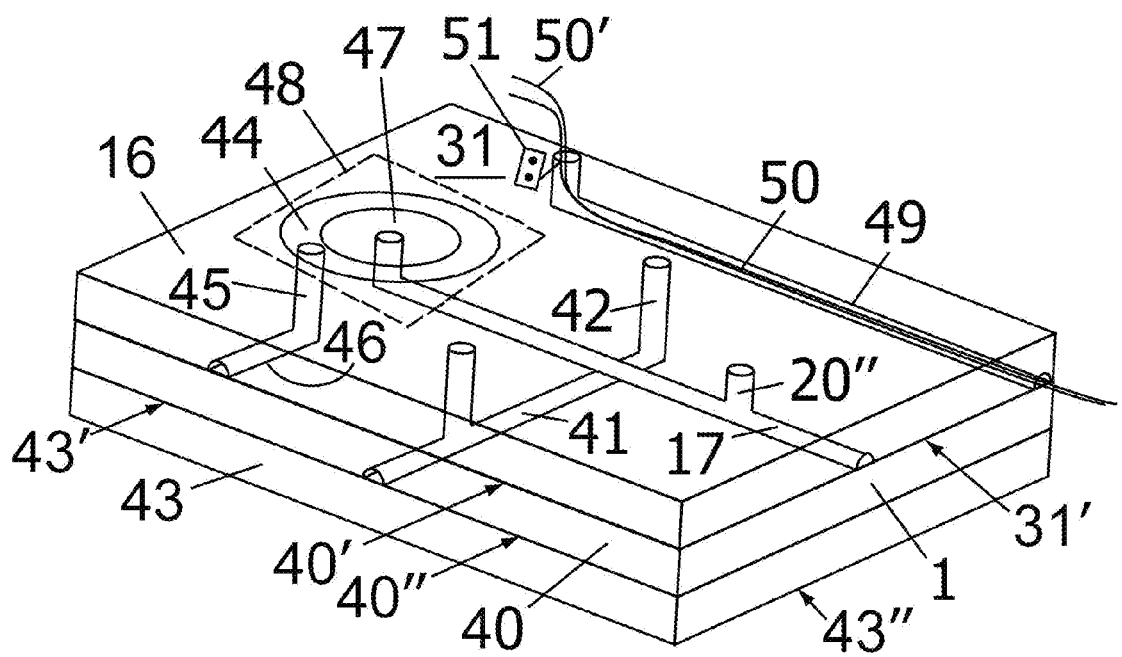
FIG. 11 is an isometric, partially cutaway view of an alternative embodiment of the present invention wherein there is provided a top plate having a grooved underside, a grooved underlying plate with grooves formed to provide jumpers around and between grooves of the top plate, and a bottom sealing plate.

Referring to FIG. 11, yet another variation of the present invention consists of forming a base 1 fused with multiple plates including a top plate 16 having an outer 31 and inner surface 31', the inner surface 31' having a pattern of grooves 17 formed thereon to form conduits for the transport of fluids and access apertures 20", for diverting fluid from said grooves 17 to the outer 31 surface of the top plate 16, a middle plate 40, having first 40' and second 40" opposing surfaces, with fluid conveying grooves 41 etched to said lower 40" surface, and access apertures 42 connecting said grooves with the outer 31 surface of top plate 16, or alternatively selective grooves 17, and can be used to form internal jumpers which can cross around grooves in the first plate without intersecting said grooves, in order to connect to specific conduit (grooves) or access apertures in the base.

A bottom plate 43 is provided to enclose the open grooves 41 (for fluid conduits) formed in the lower surface 40" of the middle plate 40, which grooves are sealed via the inner surface 43' of the bottom plate 43. Also, it is noted that the access apertures 42 could also be formed to provide fluid access from grooves 17 or 41 to the outer surface 43" of bottom plate, or to form a jumper to provide a conduit from the outer surface of the top plate to the outer surface of the bottom plate, for the mounting of modular conditioning components thereupon. This multi-plate stacked configuration (which is fused in the manner earlier described) provides, in effect, a three dimensional fluid array, or the use of jumpers from one conduit to another not possible with just two plates (without an external component).

An additional feature which may be provided is a system for fluid passages to surround areas where fluid leaks may potentially occur, such as connection points between a sample conditioning component and the surface of the fused base board in a manner that, should a fluid leak occur, it will be captured and routed to a suitable location.

As shown, a capture groove 44 is formed to surround, in spaced fashion, an access aperture 47 to be contained. A drain port 45 is formed through the plate to engage the capture groove and drain fluids therefrom. The drain port could pass through the plates forming the base to the opposing outer surface for collection, draining, or sensing, or could communicate with a secondary groove 46 or passage.

This approach provides safety when dealing with flammable and/or toxic fluids and will provide a means to capture and monitor for leaks. For example, an inadequate seal (for example, a faulty o-ring or gasket) of a modular sampling component mounted to engage the access aperture 47 (footprint of the modular sampling component shown as 48) could result in fluid leakage, which would be contained by capture groove 44. Thus, upon mounting a modular conditioning component to said docking surface at a mounting area (designated by footprint 48), so as to provide a mounted modular conditioning component, the modular conditioning component engages said access aperture, while enclosing said fluid containment groove, so as to form a fluid containment passage to contain any leakage from said access aperture.

To further facilitate the mounting of modular sampling components to the board, the footprint 48 of each component, along with an identifier for said component, could be imprinted to the mounting surface, to identify the mounting area of said component and assist in the positioning of said component during the mounting process. In addition, the fluid paths of said board can be traced by way of painted or etched lines and symbols similar to the methods utilizing in electronic circuit boards on the outer surface for reference in assembling or installing a system.

As indicated, the leaking fluid captured as described may be visually or electronically monitored by several current art techniques. Also, it is noted that, ideally, a secondary seal such as an o-ring or gasket is provided about the capture groove 44 (and between the component and the board) to further contain possible leakage.

Thus, the above design thereby provides fluid conduits around other conduits (i.e. grooves) to complete the desired fluid conditioning circuit, providing a means for "jumping"

passageways and also provide options for conditioning component fluid interconnections (such as leak containment) not otherwise possible. It can also facilitate the docking of conditioning components on two sides of a fused or bonded plate sandwich, for producing a more compact structure.

Continuing with FIG. 11, it is noted that the conduits formed via the grooves (for example 17, 41 and access apertures 42, 47) are not limited to conveying fluids. As shown, a conduit 49 for conveying wire, fiber optic cable, or other medium 50 may likewise be provided to convey the wire within the base and to the outer 31 mounting surface via access aperture 42 or port to engage a modular conditioner component mounted thereupon. The connection may be via the ends 50' of the medium wired into the component, or may be via a conductor junction 51 or the like. The conduits formed in the base could also be formed to contain medium such as resistance-type heater wire, heat pipes, or cooling or heating fluids, which could be useful to heat or cool the base and/or sample fluid(s), depending upon the application.

The conductor junction may be provided adjacent to the fluid access apertures formed on the mounting surface of the base, so that a modular sampling component can mount simultaneously to engage fluid via the access apertures (i.e., 42), as well as communications, power or the like via an adjacent conductor junction 51, which, like the fluid conduits, ideally would on the mounting surface of the base, within the footprint 48 (which footprint could be printed on the board for reference) of the modular component to be mounted.

As earlier indicated, the access aperture(s) could be surrounded by leak containment means such as the capture groove 44. In such a situation, ideally the conductor junction 51 could be provided outside of the capture area of the capture groove, so ensure that the conductor junction is kept dry in the event of a leak.

Another means presented in this invention for "jumping" passageways is the use of a "jumper block," which when mounted on the component docking surface, provides an external, above the docking surface, means for jumping over integral, internal passageways.

Figure 8:
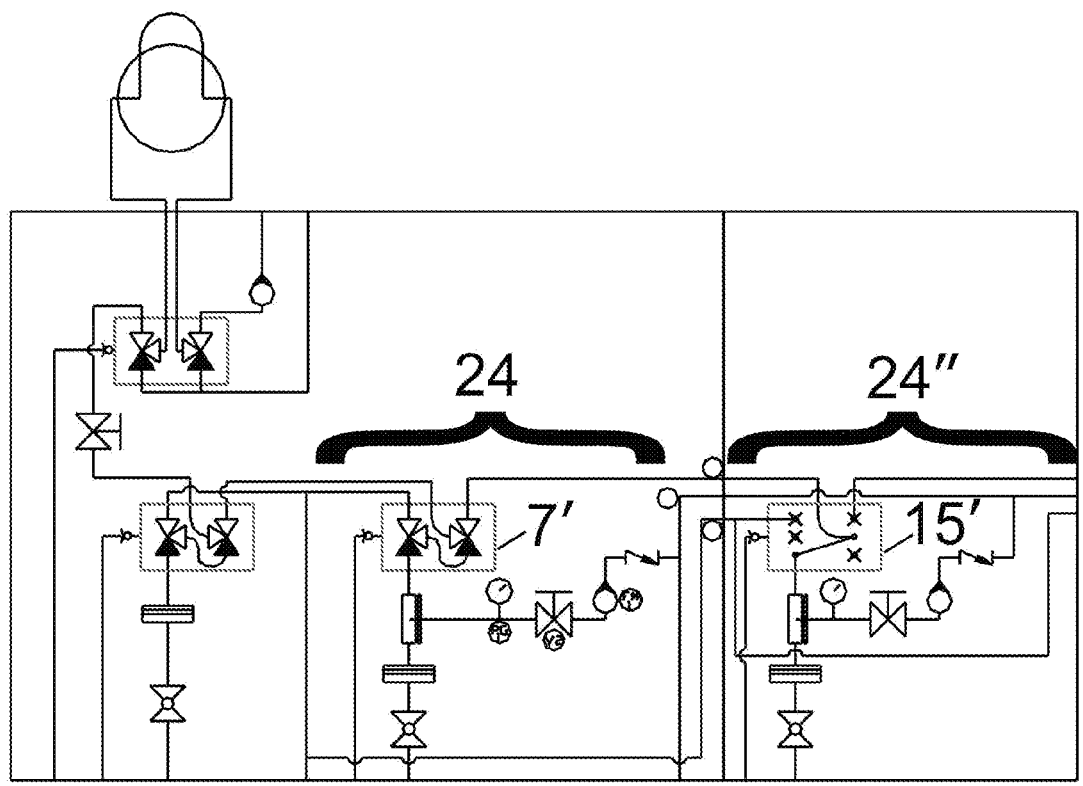
FIG. 8 illustrates a first modular board fluid schematic formed configured for calibration gas and two sample streams, with passageway jumpers to accommodate a future, adjacent modular board.
Figure 9:
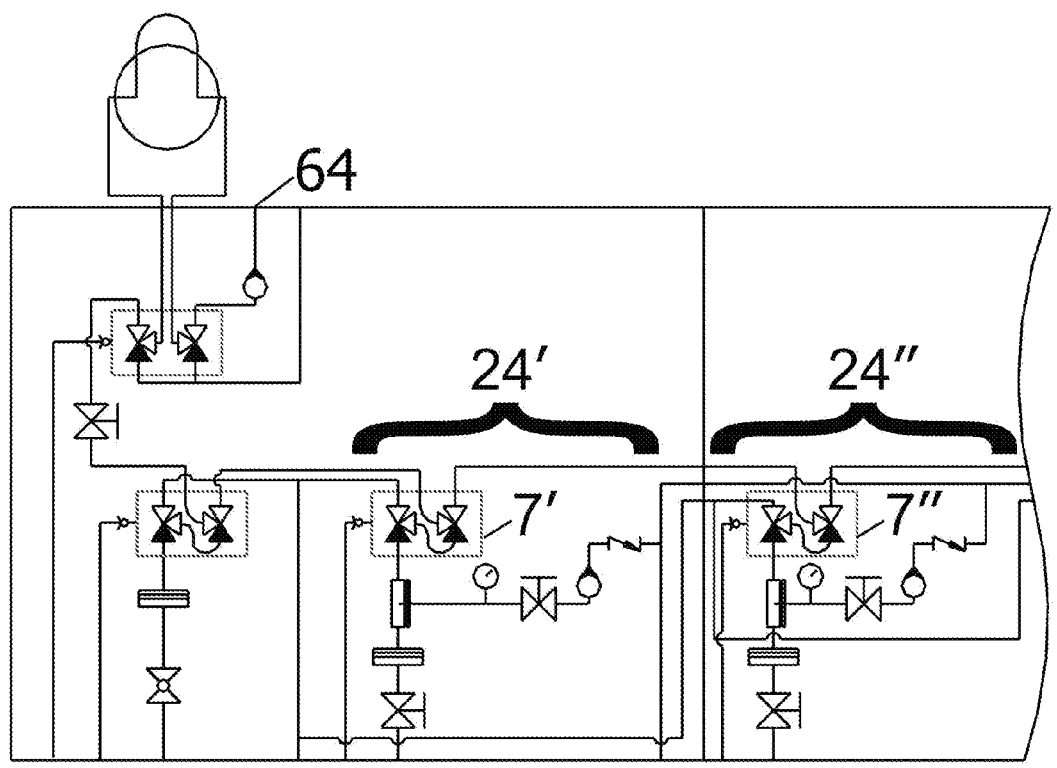
FIG. 9 is a second modular board fluid schematic formed for a calibration gas and multiple sample streams, with only two sample streams shown (plus calibration and actuation streams).

See, for example, the discussion of FIGS. 8 and 9. In a similar manner, several fused base boards, each containing essentially all components and interconnection passages for proper conditioning of sample fluids may be linked by jumpers in fluid communication with passages of two or more fused base boards.

The construction of the present invention is unique, even thought it utilizes a well known bonding technique, in the sense that employing the bonding and passage forming grooving technique produces a near ideal structure for sample conditioning not contemplated by the prior art.

The utilization of the jumper technique allows a customer to expand the capabilities of an installed system as required. For example, the customer might be utilizing certain of the passageways in the baseboard for interconnecting several installed system components. But the base may contain additional unused passageways which may be tapped via an added jumper block, which could be used to install additional components for additional features, or to reconfigure a system for different capabilities or uses. Thus, it is easy to add streams. Further, a single jumper may be utilized to provide a connection between two bases for expansion as required.

Figure 1A:
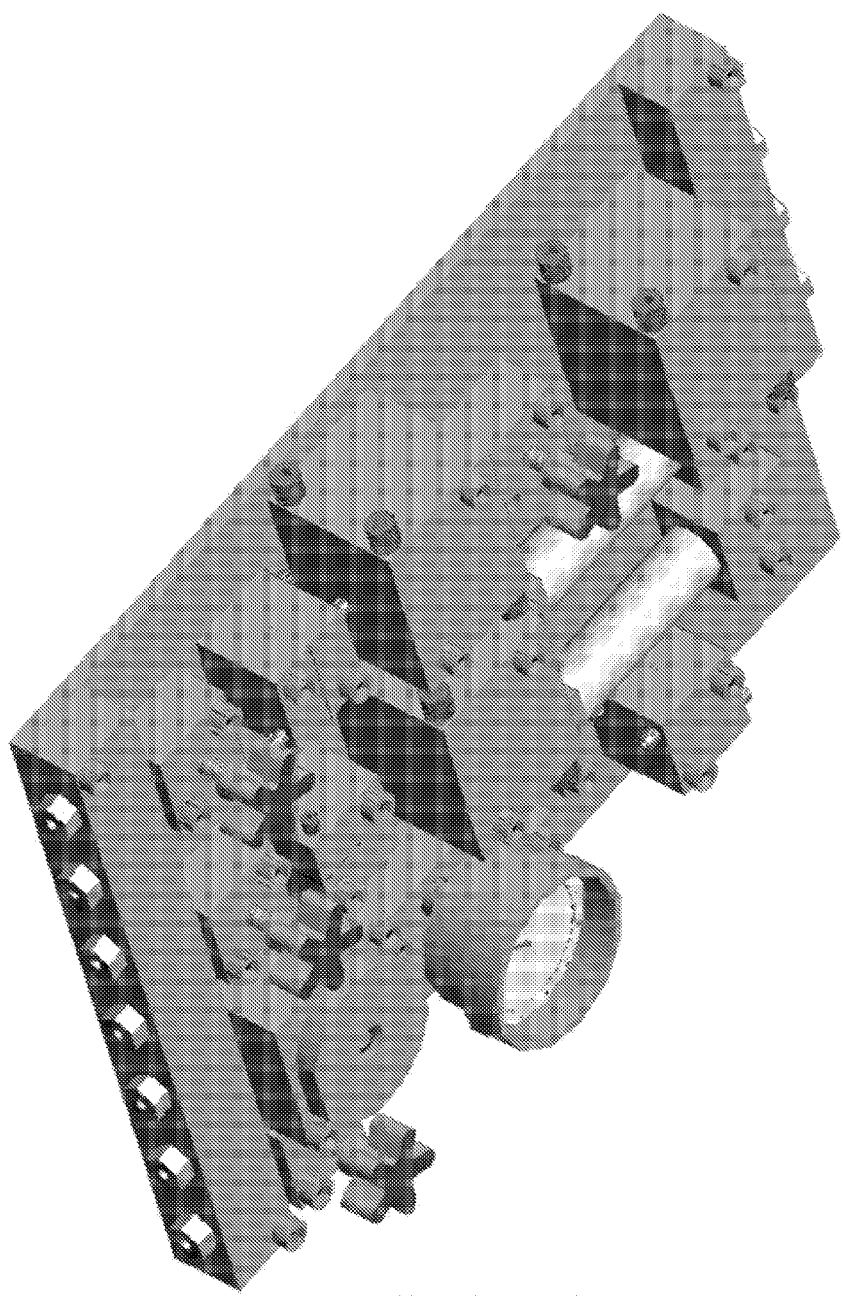
FIG. 1A is an isometric, solid view of the invention of FIG. 1.

FIGS. 1 and 1A illustrate a plurality of fluid conditioning component modules mounted to a single modular base 1, which could be formed of first and second fused plates in the manner discussed above. Low volume fittings (LVF) may be utilized for tubing connections to and from the modular base, such as, for example, at fluid input 13 and output 12 ports. The exemplary fluid conditioning component modules shown in FIG. 1 utilize the exemplary fluid circuit shown in FIG. 2.

Figure 10:
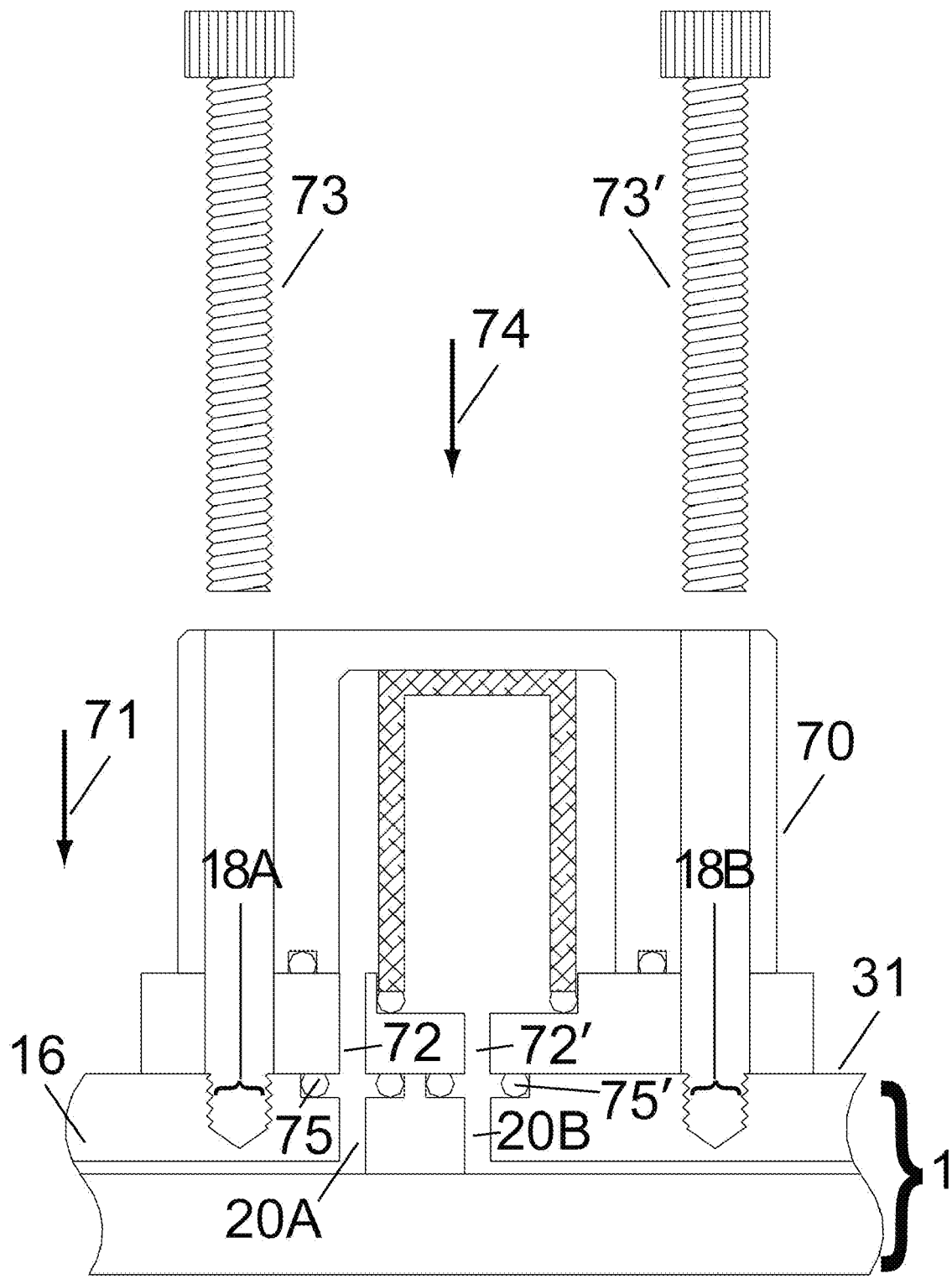
FIG. 10 is a side, cross-sectional view of a modular conditioning component mounted to the outer surface of the top plate of the modular board of FIG. 1.

FIG. 10 is a side, cross-sectional view of a modular conditioning component mounted to the outer surface of the top plate of the modular board of FIG. 1. In the present example of the invention, each modular sampling component (a filter component 70 is illustrated in this example) is mounted 71 upon the outer surface 31 of the top plate 16 (forming the junction surface) of the base unit such that the access apertures 72, 72' on said components are aligned with predetermined access apertures 20a, 20b or ports on the base. As indicated, fasteners, such as threaded fasteners 73, 73' or the like may be inserted 74 through the component and engage mounting apertures 18a, 18b formed in the base to affix said component to the base. Standard o-rings 75, 75' at the fluid port connections between the mounted components and the access apertures at the base can be utilized to provide reliable, leak free connections, while reducing cost; also, this ensures an availability of a wide range of elastomers to fit most needs. It is noted that, while an indentation is shown in the base to accommodate the o-rings 75, 75', said o-rings could similarly be mounted in the modular component via o-ring indentation formed about the access apertures 72, 72', so that the base mounting surface could be flat.

Figure 12:
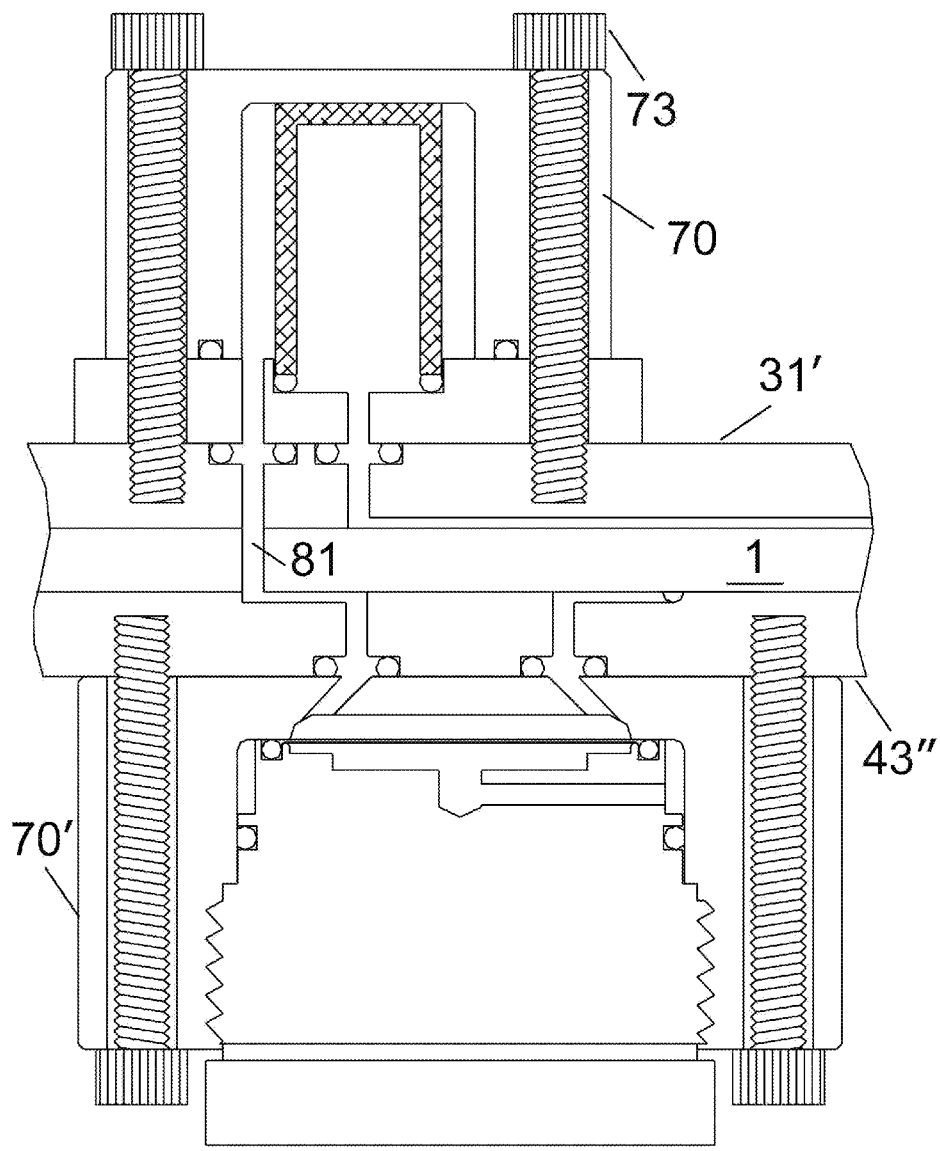
FIG. 12 is a side, cross-sectional view of first and second modular components mounted to opposing sides of a multi-plate stack of plates forming a modular board or base.

While the present invention has up to now illustrated the mounting of the modular conditioning components to a single side of the base, one may also design the base to provide for mounting components to both outer surfaces in the manner shown in FIG. 12. Such a configuration could provide double the surface area for the mounting of the conditioning components, resulting in half the footprint or size requirements of a base having a single mounting surface.

As shown, the base of FIG. 12 has opposing mounting surfaces (comprising the outer surfaces 31', 43" of the top and bottom plates of a multi-plate base of FIG. 11, respectively), which have modular sampling components mounted thereto and function in a manner consistent with the discussion of the single sided junction surface of FIG. 10 above, but utilize with a base which has been configured to have access ports on both sides for the mounting of the conditioning components thereto. A three-plate system consistent with the teachings of FIG. 11 is shown as the exemplary base, although it is envisioned that even two plate bases could be utilized in this capacity, depending upon the flow configuration required. As shown, first (the filter component 70 of FIG. 10) and second (shown as a membrane gas separator 70') conditioning components are mounted to opposing sides of the base, the first and second components communicating fluid in this example via the use of an jumper passage 81.

Figure 2:
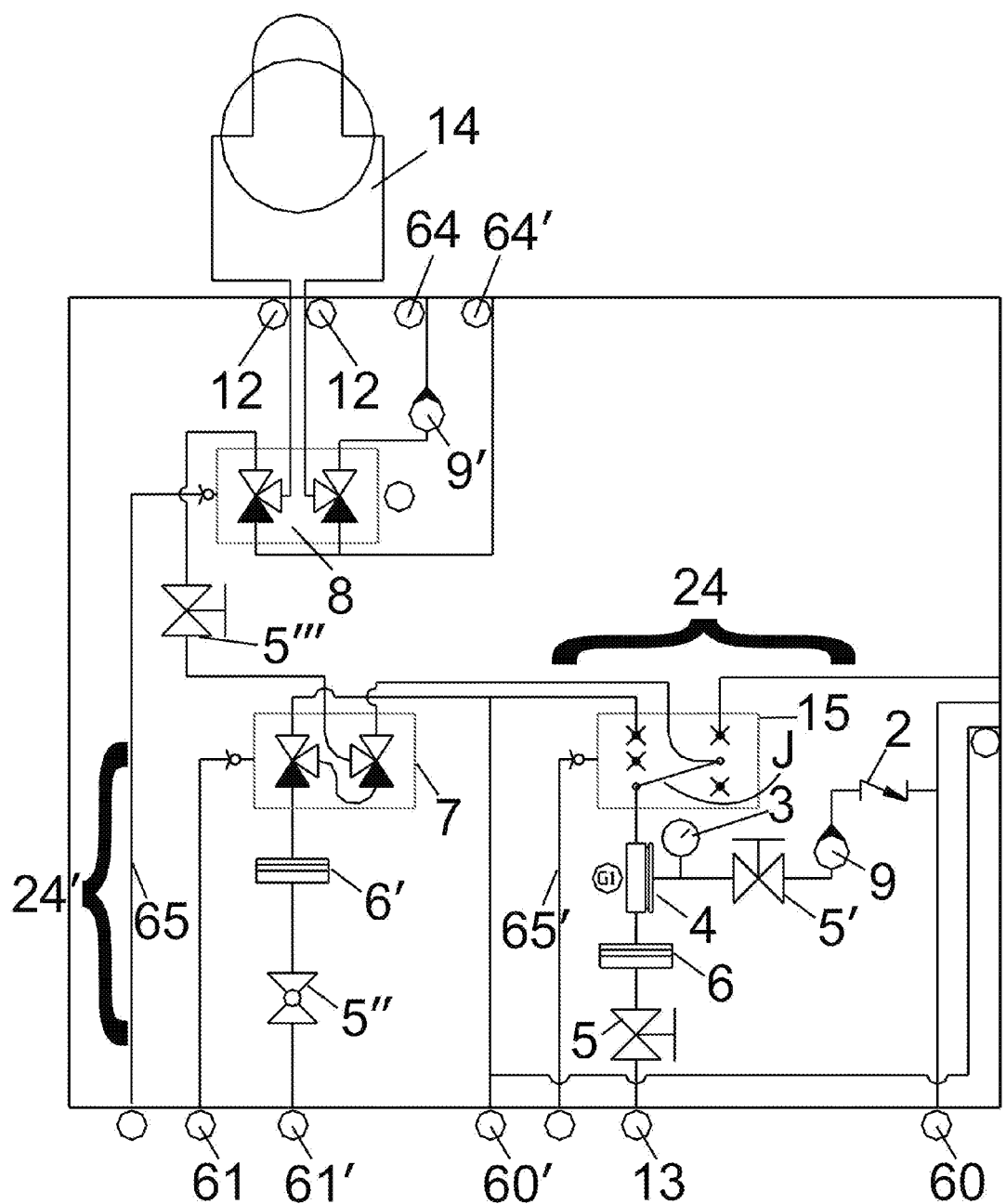
FIG. 2 is an exemplary fluid circuit schematic of an exemplary modular board if FIG. 1, configured for calibration gas, actuation of stream switching valves (via actuation gas stream), and a single sample stream.
Figure 3:
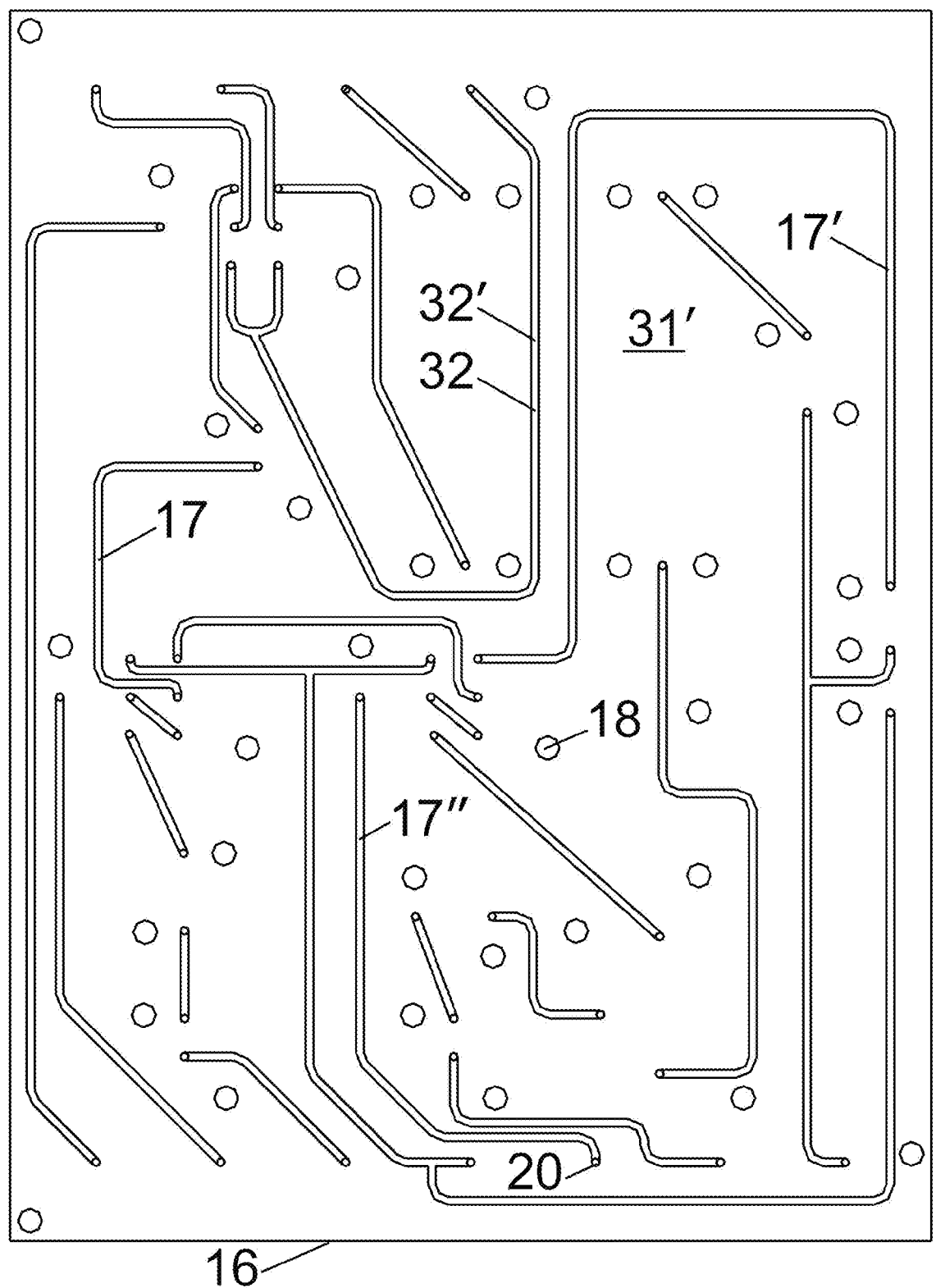
FIG. 3 is an isometric view of the lower surface of the top plate of the fluid modular base of FIG. 1.
Figure 4:
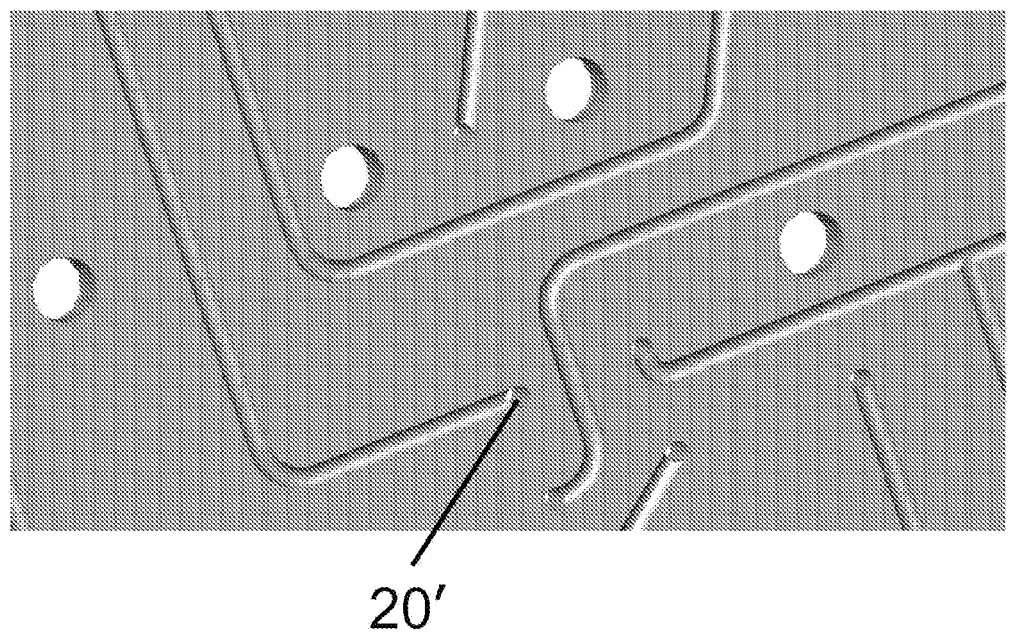
FIG. 4 is an isometric, close-up view of the lower surface of an exemplary top plate, illustrating the grooves upon the inner surface as well as apertures formed to communicate with modules mounted to the top surface of the top plate.

Referencing the schematic of FIG. 2 and the drawing of FIG. 1, an example of the present system, with modular sample conditioner components installed for a single stream 24 and separate calibration gas 24' input, is provided. As shown, fluid is directed into the system via fluid input port 13 (at the fluid input manifold 10) where it flows through valve, 5, filter 6, membrane separator 4, where gas filters through on to pressure gauge 3, valve 5', flow meter 9 (i.e. rotometer), check valve 2, and out through common bypass outlet 60.

Fluid separated by the membrane separator 4 forms the sample stream which then passes through a jumper plate 15, which comprises first and second sets of three ports each. While ordinarily a valve would be provided, because there is only a single process stream in the present flow diagram, a less expensive jumper plate 15 may be used instead, with a jumper J directing the sample stream flow to stream switching or selection valve 7.

Calibration gas inputs at 61' passing through valve 5", filter 6', to the calibration stream switching valve comprising a selection valve 7 (shown as dual three way valves), which function as a selection valve to select between the sample stream stream, or the calibration stream.

Fluid passing through the selection valve 7 is then directed to pass through valve 5'" through the SSO ARV Valve 8. The SSO ARV valve (Sample Shutoff, Atmospheric Reference Vent), flow is generally configured to operate in a non-actuated position, wherein the fluid passes up via port 12' through analyzer sample valve 14, then back through port 12 to valve 8, where it is directed through flow meter 9' (i.e., rotovalve) to analyzer vent 64.

The SSO ARV Valve 8 can be actuated via actuation air 65 to energize valve 8, so as to place the flow through the analyzer sample valve 14 in an equalization mode, wherein the sample flow to analyzer sample valve 14 is interrupted and the pressurized contents thereof are diverted through atmospheric vent 64', effectively equalizing the sample in the analyzer sample valve to atmospheric pressure.

In the alternative exemplary fluid schematic of FIG. 8, the jumper plate 15 of FIG. 2 is replaced with a selection valve 7' at the first sample stream to provide switching between first 24 and second 24" sample streams, with the second sample stream utilizing a jumper plate 15' with a jumper instead of a valve to direct the sample fluid flow to selection valve 7'.

Unlike the single stream analyzer flow diagram of FIG. 2 or the two sample stream diagram of FIG. 9 illustrates two streams, with the jumper plate (15' in FIG. 8) at the second stream replaced with a selection valve 7" to provide the capacity to handle more than two sample streams (via inputs situated right of the second stream 24" side as shown in the flow schematic).

Thus, fluid connection can be provided between a first base module and a separate, second base module, each said base module containing multiple sample conditioning components to increase capacity or provide various functions unavailable with a single base module, and the connections can be via fluid conduits along the edges of the base module, or via jumpers or the like at the docking surface of a first base board module to a docking surface of said second base module, or visa versa.

By utilizing the technique of the modular base of the present invention upon which the components are mounted, one eliminates the requirement for tubing and pipe fitting for interconnection, thereby eliminating a major source of leaks, as the fluid passages are formed internal to the modular base, providing a compact footprint which minimizes internal volume and eliminates "dead volume".

In summary, an exemplary method of sample conditioning of the present invention can be summarized in the following steps:

A. Establishing a fluid communication order of sample conditioning components to effect conditioning of said sample fluid;

B. Designing a system of fluid passages to fluidly interconnect said sample conditioning components;

C. Forming said fluid passages by forming grooves on a first surface of a first base plate;

D. Sealing said formed grooves in said first base plate to provide enclosed fluid passages by sealing a second plate over said grooves;

E. Providing fluid communication of said enclosed passages with the outer surface of one of said first or second plates via junction ports, said junction ports positioned so as to form a component docking surface; and F. Mounting said sample conditioning components to said component docking surface so as to communicate with said enclosed fluid passages in the fluid communication order of Step "A".

As earlier discussed, multiple base modules may be arrayed in serial or parallel by providing a fluid connection (such as a jumper) between said first base module and a second base module, each said base module containing multiple sample conditioning components.

Suitable methods of sealing the second plate over the grooves formed in the first plate in fluid impermeable manner include brazing (for example, nickel brazing), adhesive bonding, fusion, or solvent bonding, utilizing known techniques.

Suitable methods of forming the grooves in the first plate could include, for example, mechanical milling, chemical etching, laser etching, and the like utilizing available third party machinery and known techniques. It is noted other steps, such as plating of the grooved surfaces, may be desirable to resist chemical attack or chemical adsorption, utilizing techniques and formulations known in the art. Also, one or more passages could be provided for actuation fluid.

As earlier indicated, the passages may be provided not only for fluidic passage but also as a conduit for electrical and/or electronic wiring or communication cable, so the system is not intended to be limited for fluid passageways, but to provide communication of fluid, power, and communications in modular base connection to modular system components mounted thereon.

Exemplary Specifications

Board size:

Board material:

Plate dimensions:

Groove depth:

Groove width:

Access aperture diameter:

The following element list, which summarizes the discussion of the invention above, should be viewed in conjunction with FIGS. 1-12:

J Jumper
1 Modular base
2 Check valve
3 Pressure gauge
4 Membrane separator
5 Valve
6 Filter
7 Stream switching (selection) valve
8 Sample shut off/atmospheric reference vent valve
9 Flow meter
10 Fluid input manifold
11 Fluid output manifold
12 from external sample injection valve
13 Typical fluid input port
14 Analyzer sample valve
15,' Jumper plate
16 top plate
17, 17', 17" grooves formed in inner surface of top plate
18, 18a 18b mounting apertures
20, 20', 20A, 20B Access apertures
22 Bottom plate
22' inner surface bottom plate
24. First fluid circuit
24' calibration circuit
24" second stream 25. Jumping passageways
26. Second fluid circuit
31, 31' outer surface, inner surface of first, top plate
32, 32' depth, width of grooves
33, 33' joined
40 middle plate having a first 40' and second 40" sides
41 grooves etched therein
42 access apertures
43 bottom plate, 43' inner surface, 43" outer surface
44 capture groove
45 drain port
46 secondary groove
47 access aperture
48 footprint of modular sampling component
49 conduit
50,' medium, end
51 conductor junction
60, 60" common bypass outlet
61' cal gas inlet
61 activation Gas
62 second stream
63 third stream
64,' analyzer vent, atmospheric vent
65, 65' actuation gas
70 filter component
70 gas separation membrane component
71 mounted
72, 72' access apertures in base
73, 73' fasteners
74 inserted
75, 75' o-rings
81 jumper passage The invention embodiments herein described are done so in detail for exemplary purposes only, and may be subject to many different variations in design, structure, application, and operation methodology. Thus, the detailed disclosures therein should be interpreted in an illustrative, exemplary manner, and not in a limited sense.

What is claimed is:

1. A method of providing a sample fluid conditioning apparatus, comprising the steps of:
    a. Establishing a fluid communication order of sample conditioning components to effect conditioning of said sample fluid;
    b. Designing a system of fluid passages to fluidly interconnect said sample conditioning components;
    c. Forming said fluid passages by forming grooves on a first surface of a first base plate;
    d. Sealing said formed grooves in said first base plate to provide enclosed fluid passages by sealing a second plate over said grooves, forming a base module;
    e. Providing fluid communication of said enclosed passages in said base module with the outer surface of said first plate via junction ports, said junction ports positioned so as to form a component docking surface;
    f. Mounting said sample conditioning components to said component docking surface so as to communicate with said enclosed fluid passages in the fluid communication order of Step "A";
    g. Providing fluid communication of said enclosed passages in said base module with the outer surface of said second plate via junction ports, said junction ports positioned so as to form a second component docking surface; and
    h. Mounting said sample conditioning components to said second component docking surface so as to communicate with said enclosed fluid passages in the fluid communication order of Step "A".

2. The method of claim 1, wherein there is further included the additional step "g" of providing a fluid connection between said base module and a second base module, each said base module containing multiple sample conditioning components.

3. The method of claim 2, wherein said fluid connections are from the docking surface of a first base board module to a docking surface of said second base module.

4. The method of claim 1, wherein said second plate is sealed over said grooves formed in said first plate by brazing.

5. The method of claim 4, wherein the brazing is nickel brazing.

6. The method of claim 1, wherein said second plate is sealed over said grooves formed in said first plate by adhesive bonding.

7. The method of claim 1, wherein said second plate is sealed over said grooves formed in said first plate by fusion.

8. The method of claim 1, wherein said second plate is sealed over said grooves formed in said first plate by solvent bonding.

9. The method of claim 1, wherein said grooves are formed in said first plate by mechanical milling.

10. The method of claim 1, wherein said grooves are formed by chemical etching.

11. The method of claim 1, wherein said grooves are formed by laser etching.

12. The method of claim 1, wherein said grooves are plated to resist chemical attack.

13. The method of claim 1, wherein said grooves are plated to resist adsorption of sample fluid components.

14. The method of claim 1, wherein said base module is constructed from three or more plates.

15. The method of claim 1 wherein said passages provide a conduit for electronic wiring or communication cable.

16. The method of claim 1 wherein said passages provides one or more passages for actuation fluid.

17. The method of claim 1, wherein said base plates forming said first base board module are stacked upon one another.

18. The method of claim 1, wherein in step "a" said docking surface is formed to have a mounting area for a modular conditioning component, and wherein in step "a" there is further provided the step of forming an access aperture in said mounting area, said access aperture formed to communicate with one or more of said passages formed in said base board module.

19. The method of claim 18, wherein there is further provided in step "a" the step of forming a fluid containment groove formed in said mounting area about said access aperture so as to contain and divert fluid leakage from said access aperture.

20. The method of claim 19, wherein in step "f" there is further provided the step of mounting a modular conditioning component to said docking surface at said mounting area so as to provide a mounted modular conditioning component, said mounted modular conditioning component engaging said access aperture, while enclosing said fluid containment groove to form a fluid containment passage to contain and divert any leakage from said access aperture.

21. The method of claim 20, wherein in step "a" there is further provided the step of indicating the location of said mounting area via indicia, and in step "f" there is further provided the step of utilizing said indicia to position and mount said modular conditioning component.

22. The method of claim 21, wherein said indicia indicates the type of modular sample component to be mounted thereon.

23. The method of claim 1, wherein in step "d", a gasket is juxtaposed between said first plate and said second plate to contain fluid in said grooves formed in said first plate.

24. The method of claim 23, wherein in step "d" said first and second plates are mechanically engaged to one another via threaded fasteners so as to engage said gasket about said grooves.

25. The method of claim 1, wherein in step "a" said docking surface is formed to have a mounting area for a manifold, and wherein in step "a" there is further provided the step of forming access apertures in said mounting area, said access apertures formed to communicate with one or more of said passages formed in said base board module.

26. The method of claim 25, wherein there is provided the added steps of:
   h. providing a manifold comprising a body having formed therethrough a series of passages, each of said passages having first and second ends, each of said first ends formed to engage a separate fluid line, said second ends of each of said passages positioned to align with predetermined said access apertures formed in said mounting area; and
   I. mounting said manifold to said docking surface, so as to engage said second ends of said passages formed in said manifold in predetermined manner to said access apertures in said docking surface, providing fluid communication therebetween.

* * * * *